United States Patent [19]

Delmas

[11] Patent Number: 5,618,663
[45] Date of Patent: Apr. 8, 1997

[54] DEVICE FOR PRODUCING A SUPERNATANT OF ACTIVATED THROMBOCYTES, METHOD FOR IMPLEMENTING THE DEVICE AND SUPERNATANT OBTAINED

[75] Inventor: Olivier Delmas, 14, rue Bellevue, 37250 Montbazon, France

[73] Assignees: Inoteb, St. Gonnery; Olivier Delmas, Montbazon, both of France

[21] Appl. No.: 343,605

[22] PCT Filed: Jun. 7, 1993

[86] PCT No.: PCT/FR93/00544

§ 371 Date: Jan. 13, 1995

§ 102(e) Date: Jan. 13, 1995

[87] PCT Pub. No.: WO93/25215

PCT Pub. Date: Dec. 23, 1993

[30] Foreign Application Priority Data

Jun. 5, 1992 [FR] France ..................................... 92 06826

[51] Int. Cl.⁶ ....................................................... A01N 1/02
[52] U.S. Cl. ........................ 435/2; 435/283.1; 435/308.1; 530/380; 530/412
[58] Field of Search ............................. 435/2, 70.3–70.5, 435/283.1, 286.5, 308.1, 803; 530/380–384, 412, 427, 399

[56] References Cited

U.S. PATENT DOCUMENTS

| | | |
|---|---|---|
| 4,360,435 | 11/1982 | Bellamy et al. . |
| 4,410,630 | 10/1983 | Zierdt . |
| 4,479,896 | 10/1984 | Antoniades . |
| 4,618,494 | 10/1986 | Angers . |
| 4,705,632 | 11/1987 | Yagita et al. ........................ 210/500.23 |
| 4,731,260 | 3/1988 | Balding et al. .......................... 427/236 |
| 4,760,131 | 7/1988 | Sundsmo et al. . |
| 4,931,185 | 6/1990 | Bourgeois et al. . |

FOREIGN PATENT DOCUMENTS

| | | |
|---|---|---|
| 315022 | 5/1989 | European Pat. Off. . |
| 0323842 | 7/1989 | European Pat. Off. . |
| 0349188 | 1/1990 | European Pat. Off. . |
| 2513896 | 4/1983 | France . |
| 2112293 | 7/1983 | United Kingdom . |
| 84/00905 | 3/1984 | WIPO . |
| 86/03122 | 6/1986 | WIPO . |
| 86/07279 | 12/1986 | WIPO . |
| 88/03409 | 5/1988 | WIPO . |
| 89/05656 | 6/1989 | WIPO . |
| 90/07931 | 7/1990 | WIPO . |

OTHER PUBLICATIONS

D. R. Knighton et al., "Role of Platelets and Fibrin in the Healing Sequence", *Annal of Surgery*, No. 4, vol. 196, Oct. 1982, pp. 379–387.

R. A. Terkeltaub et al., "Platelets and Response to Injury", *The Molecular and Cellular Biology of Wound Repair*, pp. 36–55, No Date Provided.

D. M. Carter et al. "Clinical Experience With Crude Preparations of Growth Factors in Healing of Chronic Wounds in Human Subjects", *Growth Factors and Other Aspects of Wound Healing: Biological and Clinical Implications*, pp. 303–317 (1988).

J. N. Linden et al., "Platelet Interaction with Artificial Surfaces: in Vitro Evaluation", *Methods in Enzymology*, vol. 169, pp. 104–117 (1989).

J. F. Mustard et al., "Isolation of Human Platelets from Plasma by Centrifugation and Washing", *Methods in Enzymology*, vol. 169, pp. 3–27 (1989).

H. L. Wong et al., "Imflammation and Repair", *Peptide Growth Factors and their Receptors*, pp. 509–548. No Date Provided.

*Primary Examiner*—William H. Beisner
*Attorney, Agent, or Firm*—Oliff & Berridge

[57] ABSTRACT

A method for preparing platelet factors features a liquid that contains a suspension of thrombocytes being passed over a filter capable of retaining the thrombocytes. Thrombocytes are activated by an activating solution that is administered to the thrombocytes retained on the filter. A filtrate containing platelet factors in solution is separated by filtration while the thrombocytes are retained on the filter.

6 Claims, 2 Drawing Sheets

5,618,663

DEVICE FOR PRODUCING A SUPERNATANT OF ACTIVATED THROMBOCYTES, METHOD FOR IMPLEMENTING THE DEVICE AND SUPERNATANT OBTAINED

FIELD OF THE INVENTION

The present invention relates to a process for the preparation of platelet factors (contents of thrombocytic granules) and to a device which makes possible the activation of thrombocytes, of human or animal origin, stored on or in a polymeric framework for the purpose of obtaining, in a short time and without risk of external contamination, soluble molecules having a biological activity.

BACKGROUND

The solution of platelet factors released by the activated thrombocytes (also known as "platelets") is often denoted by the expression "activated-thrombocyte supernatant".

Activated-thrombocyte supernatants are currently used as starting materials for the purification of biological molecules, such as, for example: platelet-derived growth factor, transforming growth factor-$\beta$, basic fibroblast growth factor, platelet factor 4, platelet-derived endothelial growth factor, heparin-binding epidermal growth factor, insulin-like growth factor 1, connective tissue activating peptide III, $\beta$-thromboglobulin, epidermal growth factor, plasminogen, Von Willsbrand factor, fibrinogen, serotonin, histamine, adenosine di- and triphosphate, fibronectin, vitronectin, factor XIII, proteolytic or glycolytic enzymes, or the metabolites of arachidonic acid (see the review, Inflammation and Repair, H. L. Wong & S. M. Wahl, in "Peptide Growth Factors and their Receptors", p. 510, edited by Sporn & Roberts, Springer-Verlag, Berlin; Platelets and Response to Injury, R. A. Terkeltaub & M. H. Ginsberg, in "The Molecular and Cellular Biology of Wound Repair", p. 38, edited by Clark & Henson, Plenum Press, New York).

Certain purification methods are known and were able to form the subject of patent filings. Mention may especially be made of: European Patent No. 89100148.9 relating to the purification of transforming growth factor-$\beta$ and U.S. Pat. No. 4,479,896 relating to the purification of platelet-derived growth factor.

Activated-thrombocyte supernatants (or a fraction of these supernatants) can be used in therapy, for example for their healing activity (D. Knighton et al., Ann. Surg. (1982) 196, 379–388; D. M. Carter et al., in: Growth Factors and Other Aspects in Wound Healing, p. 303–317, edited by Barbul, Pines, Cadwell and Hunt, Alan R. Liss Inc., New York, 1988; U.S. Pat. No. 4,760,131; Patent WO 88/03409; Patent WO 86/03122; Patent WO 89/05656), or in cosmetology, for example for their beneficial effect in controlling alopecia (Patent WO 90/07931).

Platelet factors contained in activated-thrombocyte supernatants can be used especially in the treatment of ulcers.

The methods described to date for the preparation of thrombocytic supernatants are lengthy (minimum duration of approximately 1 hour 30 minutes), tedious (because they require transfers from tube to tube, getting the centrifuging balanced, pipettings) and virtually impossible to automate and they present risks of contamination of the product by its environment (transfers of liquids in open-necked vessels) or of the technician by the product being handled, which is potentially infected by transmittable germs.

In fact, these preparation methods begin with the isolation of the thrombocytes from the blood by successive centrifugings. The thrombocytes are then washed by centrifuging to remove the plasma (Isolation of Platelets, in: Methods in Enzymology, Section I, pp. 3–27, Vol. 169, edited by Hawiger, Academic Press, London, 1989; Patent WO 86/03122, U.S. Pat. No. 4,760,131). The purified thrombocytes are then suspended in the presence of an activator. Many activators are known (Platelets and Response to Injury, R. A. Terkeltaub & M. H. Ginsberg, in "The Molecular and Cellular Biology of Wound Repair", pp. 35–55, edited by Clark a Henson, Plenum Press, New York). Three types of activators are distinguished: strong activators which are capable of inducing secretion from all the granules (thrombin, collagen, calcium ionophore A23187), intermediate activators such as thromboxane A2, ADP in the presence or absence of calcium ions, or adrenalin, and weak activators which do not induce granular secretion (serotonin). The most used activator is thrombin. Other activation methods use physical methods for the lysis of thrombocytes by successive freezings/defrostings or by ultrasound. The thrombocytic supernatant is clarified by centrifuging and/or filtration in order to remove the thrombocytic membranes and other insoluble components.

In addition, in conventional techniques, the contaminants of plasma origin are difficult to remove and the successive washings which are targeted at removing these plasma contaminants lead to a reduction in the yield of thrombocytic molecules by loss of thrombocytes or by partial activation of the latter. Finally, the plasma in which the thrombocytes are suspended is difficult to recover for another use.

The present invention makes it possible to solve the problems described and which are inherent in the current methods for the preparation of platelet supernatants, such as risks of contamination, loss of yield and the need for lengthy and problematic manipulations.

SUMMARY OF THE INVENTION

The subject of the invention is a method for obtaining a solution of platelet factors comprising a stage of thrombocyte activation by bringing into contact with a thrombocyte activator solution, and in which a solution of platelet factors released by the thrombocytes during the activation stage is collected, characterized in that a liquid containing a suspension of thrombocytes is passed through a filter capable of retaining the thrombocytes, in that an activator solution is added to the thrombocytes retained on the filter and in that a filtrate containing the platelet factors in solution is separated by filtration whereas the thrombocytes remain retained on the filter.

It should be pointed out it was not obvious to attempt to control the activation of the thrombocytes by carrying out the activation on a filter, because a spontaneous activation of the thrombocytes on the filter was normally to be expected; see, for example, J. N. Lindon et al., Methods in Enzymology, 169, 104–107 (1989).

In fact, the prior art did not suggest replacing conventional centrifuging methods by a simple filtration and it can be considered that this is in keeping with the existence of a prejudice against filtration, which it was feared causes early and spontaneous activation of the thrombocytes, preventing purification of the platelet factors, that is to say their separation from a significant proportion of the plasma constituents. In fact, in the event of spontaneous activation, the platelet factors produced, which are soluble, remain with the other plasma products passing through the filter, or pass through the filter before the aqueous washes optionally used with the aim of purification before the activation stage triggered by an activator, and, in this case, this activation stage would be ineffective because it is too late or would only make it possible to obtain the platelet factors with a very low yield.

It has now been discovered that, in fact, it is surprisingly possible, with many known filters, including commercial filters, to retain the thrombocytes on the filter without observing a spontaneous activation capable of leading to significant losses of platelet factors. The filters which are suitable can be determined by simple routine experiments. It has been discovered that it is even possible, after having retained the thrombocytes on a filter, to carry out a preliminary washing, before causing activation using an activator, without crippling loss of platelet factors. It is thus possible to obtain purified platelet factor preparations which contain only small proportions of plasma constituents.

Another subject of the invention is a device which makes it possible to implement, in a simple way, the process which has just been described. This device, which is provided in the form of a closed system which makes it possible to activate thrombocytes and to obtain, in a sterile way, a solution of platelet factors starting from a liquid containing a thrombocyte suspension, is characterized in that it comprises filtration means containing a filter capable of retaining the thromobocytes, the said filter being placed in an enclosure and delimiting, in the said enclosure, an upstream part and a downstream part, the upstream part of the said enclosure being in communication with at least one pipe, equipped with appropriate opening and closing means, connecting or making it possible to connect the upstream part to a reservoir containing the starting liquid, and the downstream part of the said enclosure being in communication with at least one pipe, equipped with appropriate opening and closing means, making it possible to successively collect the filtrate of the starting liquid and the said solution of platelet factors, and in that it additionally comprises a reservoir containing a thrombocyte activator, the said reservoir being connected to or able to be connected to the upstream part so as to make possible the introduction into the said upstream part of the activator in the form of a solution.

The device of the invention is thus preferably provided in the form of a ready-to-use kit containing the activator, either in the solution form in an appropriate reservoir or in the form of a powder, especially in the case of thrombin. In the latter case, the activator solution is reconstituted by addition to the powder of an appropriate liquid vehicle. The liquid vehicle can be a sterile vehicle contained in a companion bag. The activator solution can also be reconstituted with a conventional liquid vehicle or prepared at the time of use, sterilization being provided by equipping the pipe for conveying the activator solution with a sterilizing filter. The washing solution can be treated in the same way.

More particularly, the present invention relates to a device which makes it possible to obtain an activated-thrombocyte supernatant (12), characterized in that it consists of a filter (5) which retains the thrombocytes, the said filter (5) being connected, on the one hand, upstream to a first means (2) for conveying the thrombocytes in suspension in a liquid (15) and a second means (4) for conveying a solution of thrombocyte activators (7) and, on the other hand, downstream to a means (8) for discharging the said suspension liquid (13) and to a means (9) for recovering the said supernatant (12), it being possible to close off the said means reversibly by appropriate means (6).

The device is preferably completed by virtue of an assembly by which it is connected upstream to a means (3) for conveying a washing liquid (14), especially a buffered washing liquid which can contain an adjuvant, and downstream to a means (10) for discharging the spent washing liquid (16).

In this device, the said means for conveying the thrombocytes in suspension in a liquid and the solution of thrombocyte activators and optionally the washing liquid are tubes each connected to a reservoir intended to contain respectively the said thrombocyte suspension, the said solution of thrombocyte activators and the said washing liquid, the said discharge means each being a tube connected to a receptacle intended to contain respectively the suspension liquid of the thrombocytes after filtration and the washing liquid, the said recovery means being a tube connected to a receptacle intended to contain the activated-thrombocyte supernatant.

As the device according to the present invention is generally intended for a single use, use will preferably be made of reservoirs and receptacles which each consist of one or a number of simple, optionally juxtaposed, transfer bags or of syringes which are themselves also disposable. The means for closing off are clamps bearing on a pipe made of deformable medical-grade plastic, for example polyethylenes.

These devices can be completed by means for by-passing the filter in order to avoid contaminations of the filter by the contents of the bags and the means for recovering the supernatant is connected to a means intended to decrease the viral load of the supernatant.

The various liquids are conveyed preferably by gravity or by pump systems of peristaltic type, for example, and the system is closed and sterile.

As is indicated, the liquid suspension containing the thrombocytes is preferably whole blood of human or animal origin or one of the blood fractions containing thrombocytes, especially a plasma or a platelet-rich plasma.

The solution of thrombocyte activators is preferably an aqueous solution.

The device according to the present invention makes it possible to obtain activated-thrombocyte supernatants under perfect sterility conditions and at costs compatible with an autologous application.

Other characteristics and advantages of the method and device according to the invention will be revealed on reading the detailed description below and in reference to the appended drawings.

DESCRIPTION OF PREFERRED EMBODIMENTS

Figure 1:
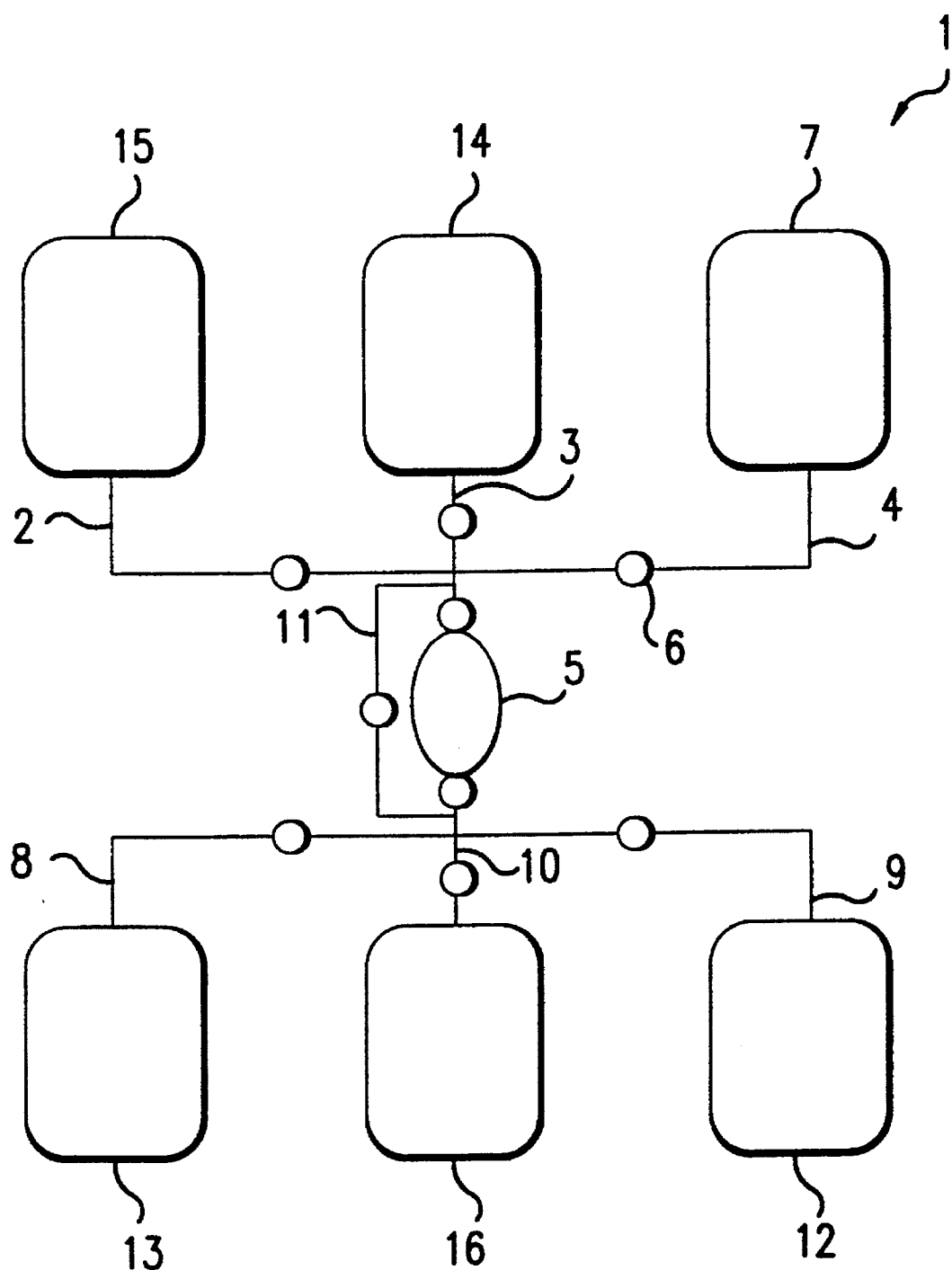
FIG. 1 schematically represents a specific embodiment of the device of the invention.

The device (1) of the present invention makes it possible to obtain an activated-thrombocyte supernatant like that described in FIG. 1.

A filter (5) intended to retain the thrombocytes constitutes the central part of the device. The filtration system can consist, for example, of a depth filter or a microporous filter. Filtration can be frontal or tangential.

A system for depth filtration can, for example, consist of a non-woven polyester filter intended to remove leucocytes from globular concentrates (Erypur Optima G-0 and G-2 filters from the Company Organon-Teknika, Fresnes, France; Pall RC100 and RC50 filters, Pall Biomedical, Paris; Sepacell R500 filters, Asahi Medical, Frankfurt/Main, Germany). According to their characteristics and their use, these systems retain from 50% to 100% of the thrombocytes. Other filter media designed particularly to retain thrombocytes are known (Patent EP-315,022).

Figure 2:
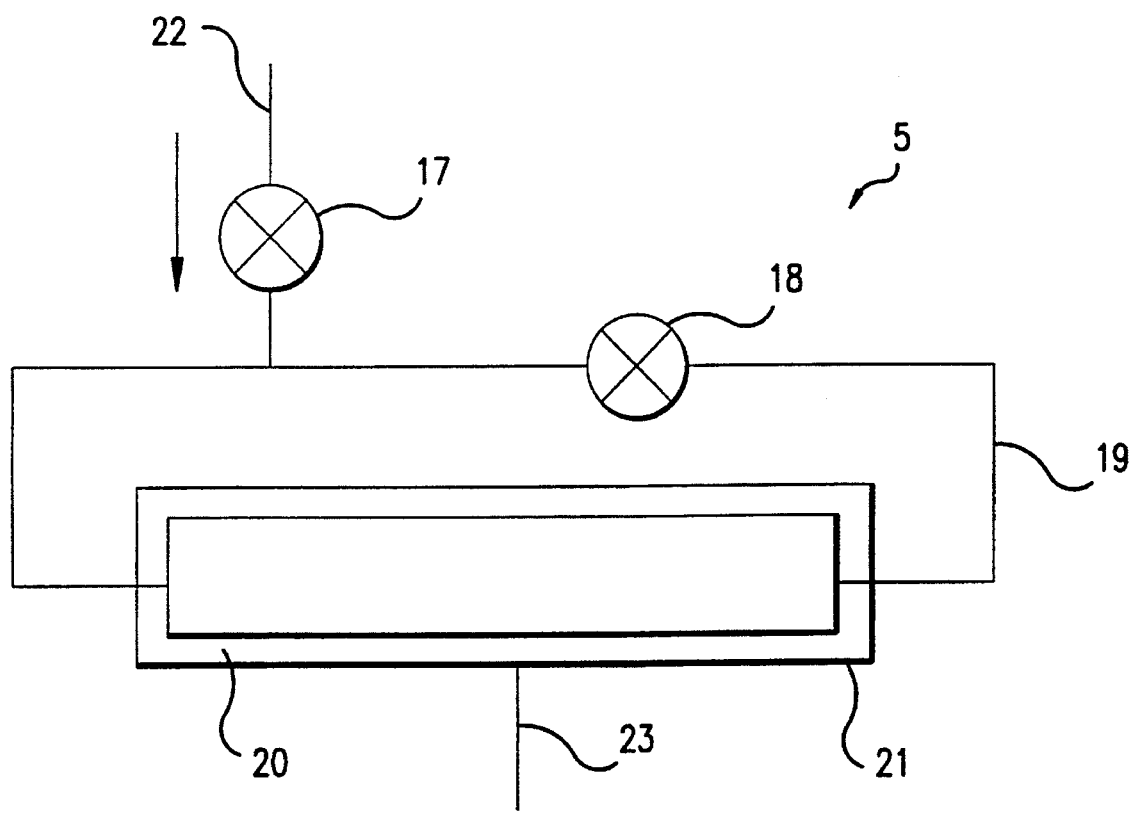
FIG. 2 schematically represents a specific embodiment, described in Example 6 below, of the filter system.

A microporous filtration system can be, for example, a cartridge (21) of hollow fibres (20) (A/G Technology, Microgon, Gambro, Enka, Patent EP-116626 cartridges) as described in FIG. 2. Filtration through microporous media is carried out, for example, tangentially. In order to carry out tangential filtration, a pipe (19) is connected to the two ends of the fibres (20). A pump, for example peristaltic (18), in combination with this pipe, provides for circulation of the retentate in the filter fibres. A pipe (22) equipped with a pump, for example a peristaltic pump (17), and connected to the pipes upstream and at (19) makes it possible to convey the solutions to be filtered towards (19). A pipe (23) connected to the cartridge (21) constitutes the outlet of the filter.

This filter (5) is connected upstream by a conveying means (2) to a receptacle containing a biological liquid (15) containing suspended thrombocytes, which liquid can be platelet-rich plasma, buffy coat, standard platelet concentrates or unitary platelet concentrates.

The filter (5) is also connected upstream by a conveying means (3) to a receptacle containing a solution of thrombocyte activators (7). The activator can be thrombin, adenosine diphosphate, collagen or calcium ionophore A 23187.

The filter (5) is additionally connected downstream by a discharge means (8) to a receptacle which receives the biological liquid (13) which contained the suspended thrombocytes. It is also connected by a recovery means (9) to a receptacle which receives the activated-thrombocyte supernatant (12).

It is possible to add, to this device, a means (3) for conveying a liquid (14) for washing the thrombocytes, the spent liquid (16) being discharged by the discharge means (10) into a receptacle intended to receive it.

The reservoirs and receptacles containing (15), (14), (7), (8), (13), (16) and (12) are, for example, transfer bags such as the flexible transfer bags commonly used in collecting blood products. Each of the conveying and discharge means can be a pipe. Each pipe can be closed off using a clamp, for example.

All the components of this device form a closed circuit (bags, pipes, needles, connectors, filters, solutions) which can be sterilized before use by appropriate means.

One of the modes of use of the device is the following:

The pipes (3), (4), (9) and (10) are closed off. The container containing the suspended thrombocytes (15) is emptied by gravity (or by a pumping system having the principle of squeezing the pipe or the bag to be emptied or the use of sterile syringe pistons) through the filter (5) into the collecting bag (13). The pipes (2) and (8) are closed off. The pipes (3) and (10) are released. The washing solution (14) is discharged by gravity after passing through the filter (5) into the bag intended to receive the spent washing solution (16). The pipes (3) and (10) are closed off and the pipes (4) and (9) are released. The bag (7) is emptied by gravity and the supernatant obtained (12) is collected in a bag. All the pipes are then closed.

In the case of the use of a tangential filtration system, a peristaltic pump (17) conveys (15), (14) or (7) towards the pipe (19). A peristaltic pump (18) on (19) provides for recirculation of the retentate in the filter fibres. The peristaltic pumps are in motion throughout the whole of the operations described in the preceding paragraph.

Certain variants of this device are possible. Mention may be made, as examples, of the following variants:

a) A pipe for by-passing the filter including a blocking device (11) can be added in order to purge the filter or in order to prevent part of (15), (14) or (7) from flowing onto the filter. For example, whole blood can be centrifuged in a syringe, the orifice of the syringe connected in place of the bag containing (15), the erythrocytes sedimented in the syringe forced into the by-pass and the supernatant plasma forced through the filter.

b) Collection of (16) can be carried out in the collecting bag for (13).

c) The bag for collecting the supernatant (12) can contain an excipient of any nature whatever, in order either to enrich the platelet supernatant, for example with healing adjuvants or with stabilizing agents, or in order to dilute the supernatant into given proportions.

d) Each of the bags can be equipped with various devices, such as sampling sites.

e) The bag for recovering the supernatant (12) can be completed by sampling points or else connected to smaller bags so as to make it possible, in a closed circuit, to distribute in a way compatible with the use of the product during a long-term treatment. Pipe connectors can be created sterilely by means of welding devices known for producing any design of sterile arrangements suitable for the mixing, separation and distribution operations.

f) The supernatant (12) can be subjected to a viral inactivation stage, either by pasteurization by immersion in a water bath under validated conditions, or by neutralizing antibodies, or by filtration (Virosolve system developed by Millipore, Bedford, USA; Asahi system, Pall system), or by any other method which is effective in decreasing the vital load while retaining a sufficient activity in the treated product. The viral inactivation system can be produced so as to be made integral with the device described above and consequently to retain the closed nature of the said device.

g) A matrix specifically retaining certain molecules of the thrombocytic supernatant can be mounted upstream or downstream of the bag for collecting the supernatant (12), in order to carry out a direct purification stage of biological molecules.

Generally, any device can be added insofar as it retains the closed nature of the system.

The present invention is illustrated by the following examples where the numerals from (1) to (16) refer to FIG. 1 and the numerals from (17) to (23) refer to FIG. 2.

Example 1 a- A 400 ml transfer bag (Baxter, reference R2074) is sterilely filled with 350 ml of a 0.04M Tris, HCl, pH 7.4, 0.15M NaCl solution (14).

b- An identical bag is filled with 250 ml of the same solution and enriched with 1250 NIH U of bovine thrombin (Roche, reference 07 2846 2) (7).

c- After having clamped all the pipes, an Optima G2 filter (Organon Teknika, Fresnes, France) is connected under a sterile atmosphere by its red upstream end to a mixture of 5 standard platelet concentrates (15) contained in a transfer bag of the same type as in a-.

d- The white upstream end of the filter is connected to the bag containing (7). The filter is manufactured to contain downstream two transfer bags numbered 1 and 2 which are used respectively to collect one (12) and the other (13) and (16).

e- The bag containing (15) is raised by 5 to 50 cm and the bag 2 is lowered with respect to the filter by the same height.

f- The pipes (2) and (8) are released. The plasma (15) flows into the bag (2) over 10 minutes, plus or minus 5 minutes.

g- The pipes are again closed off.

h- The bag which has contained (15) is removed under a sterile atmosphere. The bag containing (14) is connected in place of the bag which has contained (15). The operations as described in e, f and g are repeated.

i- The pipes (4) and (9) are released and the operations as described in e, f and g are repeated.

j- The pipe (9) is then closed by welding and cut.

At the beginning, (15) contains $318 \times 10^9$ thrombocytes in 243 ml of plasma. After the handling operation, (15) and (16) contain $13.65 \times 10^9$ thrombocytes. The filter has consequently retained 95.7% of the thrombocytes.

The results of the analyses carried out on (12) are recorded in Table I.

Thrombin can be replaced by an equivalent ADP solution.

Example 2

The device is prepared and used as in Example 1, with the following modifications: (14) has a volume of 400 ml of buffer and the bag containing (15) is an 800 ml transfer bag (Fenwal, ref. R053) filled with a mixture of three platelet-rich plasmas. The contents of the bag 2 (13) are continuously transferred during the filtration of the plasmas into an attached 800 ml bag connected to the bag 2. After filtration, (14) is emptied through the filter into the bag 2.

At the beginning, (15) contains $198.6 \times 10^9$ thrombocytes in 782 ml of plasma. After the handling operation, (13) and (16) together contain $14.4 \times 10^9$ thrombocytes. The filter has consequently retained 96.5% of the thrombocytes. The results of the analyses carried out on (12) are recorded in Table I.

Example 3

The device is prepared and used as in Example 1, with the following modifications: (14) has a volume of 360 ml of buffer and the bag containing (15) contains a mixture of three leucocyte/platelet concentrates (or buffy coat) (15).

At the beginning, (15) contains $125 \times 10^9$ thrombocytes. After the handling operation, the bag 2 containing (13) and (16) contains $4.8 \times 10^9$ thrombocytes. The filter has consequently retained 96.16% of the thrombocytes.

The results of the analyses carried out on (12) are recorded in Table I.

This example shows that, with the method of the invention, it is possible to remove a high proportion of the plasma proteins, even starting with a leucocyte/platelet concentrate. It is recalled that a plasma contains at least approximately 0.3 g of free proteins per billion platelets.

Example 4

The device is prepared and used as in Example 1, with the following modifications: the bag containing (14) contains 464 ml of a Hepes (12 g/l), NaCl (5.8 g/l), glucose (5.4 g/l), KCl (0.25 g/l) buffer (14) and the bag containing (7) contains 221 ml of the same buffer enriched with 221 U of human thrombin (7).

The total duration of the handling operation is 36 minutes, including 7 minutes for the filtration of the standard platelet concentrates, 14 minutes for washing the filter (flow of (14)) and 10 minutes for activation of the thrombocytes (flow of (7) through the filter (5)). 98% of the thrombocytes are retained on the filter.

The results of the analyses carried out on (12) are recorded in Table I.

Example 5

The following arrangement is prepared: a Sepacell R-500B1 filter (Asahi) is connected upstream and downstream, using an SCD IIB apparatus (Du Pont), to a three-way adapter equipped with closing devices and with perforators. Six 400 ml bags (Baxter, ref. R 2074) are fitted one by one onto each perforator so as to produce the device described in FIG. 1. The bags placed downstream and intended for collecting (12), (13) and (16) are empty. (15), contained in one of the upstream transfer bags, is a mixture of five standard platelet concentrates. (14), contained in the second upstream transfer bag, consists of 447 ml of the Hepes buffer described in Example 4. (7), contained in the third upstream transfer bag, consists of 245 ml of the same buffer enriched with 245 U of human thrombin.

The filtration, washing and activation operations are carried out in a similar way to the operations described in Example 1.

As the whole of the device is entirely enclosed, the handling operation is carried out entirely outside a sterile atmosphere.

The total duration of the handling operation is 41 minutes (including 7 minutes for the filtration, 11 minutes for the washing and 12 minutes for the activation).

The filter retained 89% of the thrombocytes.

(13) contains 175 ml of plasma depleted in platelets, i.e. 87.5% of the total volume of filtered plasma.

The results of the analyses carried out on (12) are recorded in Table I.

Example 6

The following arrangement is prepared: a cartridge containing PF 2000 hollow fibres (Gambro) is connected to pipes so as to produce the filter system described in FIG. 2. (22) is connected to the pipes (2), (3) and (4). (23) is connected to the pipes (8), (9) and (10) so as to produce the device described in FIG. 1. (15), contained in one of the upstream transfer bags, is a mixture of three platelet-rich plasmas. (14), contained in the second upstream transfer bag, consists of 740 ml of the Hepes buffer described in Example 4. This second upstream bag additionally contains approximately 200 ml of sterile air in order to purge the system at the end of the washing operation. (7), contained in the third upstream transfer bag, consists of 450 ml of the same buffer enriched with 2000 U of human thrombin. The peristaltic pump (17) provides a continuous flow of 22 ml/min and the peristaltic pump (18) provides a continuous flow of 80 ml/min.

The filtration, washing and activation operations are carried out in a similar way to the operations described in Example 1.

As the whole of the device is entirely enclosed, the handling operation is carried out entirely outside a sterile atmosphere.

On conclusion of the handling operation, no platelet could be detected in (12), (13) and (16). The filter therefore retained all the platelets.

The results of the analyses carried out on (12) are recorded in Table I.

Example 7

A cartridge containing hollow fibres (A/G Technology) is used: porosity of 0.2 μm; internal diameter of the fibres: 0.75 mm; total filtration surface area: 0.009 m². Such a filter makes possible sterilizing filtration because it retains bacteria. The arrangement is set up as indicated in FIG. 2, except that the pump (17) is omitted. The flow of the pump (18) is 130 ml/min. The starting material is a platelet-rich plasma with a volume of 195 ml. The other materials used are the same as those described in Example 6.

The processing is carried out in a way analogous to that described above in Example 6.

Results, per billion thrombocytes: β-thromboglobulin 50.3 μg

Volume of the platelet extract collected: 156 ml

Volume of the spent washing solution: 184 ml

The washing solution contains less than 1% (0.89%) of the total amount of β-thromboglobulin contained in the platelet extract. This means that early activation of the thrombocytes during the washing operation did not take place.

Thrombin can be replaced by ADP.

Advantages of the Present Invention with Respect to Conventional Methods

The results presented in the examples make it possible to define the following advantages:

Gain in time: total duration of 30 to 45 minutes from the production of the thrombocyte-rich plasma, instead of a minimum of 60 minutes with conventional methods.

Sterility: the product of activation of the thrombocytes is obtained in a closed circuit, eliminating risks of contaminations arising from the outside.

Protection of the technician: blood or its derivatives are potentially dangerous. The technician can under no circumstances be in direct contact with the blood products.

Ease of use: the number of operations is greatly reduced. The operations are reduced to simple handling operations of transferring liquids in a closed circuit.

Minimum equipment investment: protected or sterile enclosures are not required (savings in hoods, glove boxes, 10.000 class component), saving of a centrifuge and of various disposable equipment and tubes.

Final product of better quality: the thrombocytes are washed much more copiously compared with washings by successive centrifugings. The plasma proteins are consequently present at much lower concentrations. Moreover, the thrombocyte residues, retained on the filter, do not contaminate the final product.

Higher yield: especially of β-thromboglobulin and of transforming growth factor-β, due to a shorter handling time and to the absence of centrifugings which cause partial degranulation of the thrombocytes.

Better recovery of the plasma: at least 85% of the starting plasma can be recovered sterilely and used for other purposes.

Possibility of directly using whole blood or subfractions such as leucocyte/platelet concentrates, by virtue of the filters which specifically retain the thrombocytes and do not retain the erythrocytes.

This set of advantages confers on the device a particularly advantageous nature in an implementation of a preparation of activated-thrombocyte supernatant.

The applications of the product obtained by virtue of the invention are those of a platelet supernatant, for example:

The purification of molecules of thrombocytic origin (transforming growth factor-β, platelet-derived growth factor, and the like) for the purposes of research, manufacture of reagents, manufacture of active principles having a therapeutic use, or other purpose;

The manufacture of preparations having a therapeutic or cosmetological use, and in particular the preparation of adjuvants of tissue repairing, for example of skin healing;

The carrying out of an analytical test having diagnostic or prognostic use is targeted at evaluating the contents of the thrombocytic granules of an individual.

TABLE I

Results of the analyses carried out on the activated-thrombocyte supernatants obtained during the handling operations described in Examples 1 to 6 and mean of the results obtained during a series of ten handling operations carried out according to the protocol described in Patent WO 86/03122

|  | Proteins (1) μg/ $10^9$ Thr.* | β-TG (2) μg/ $10^9$ Thr. | PDGF (3) ng/ $10^9$ Thr. | TGF-β μg/ $10^9$ Thr. | Nitrogen activity/ $10^9$ Thr. |
|---|---|---|---|---|---|
| Example 1 | 75 | 67 | 17.4 | 1.6 | 44 |
| Example 2 | 151 | 60.4 | 11 | 1.7 | 32.2 |
| Example 3 | 2160 | 68.8 | 15 | 2 | 48 |
| Example 4 | 138 | 20 | 10.6 | 0.8 | 18 |
| Example 5 | 62.4 | 11 | 7.6 | 1.1 | 17.2 |
| Example 6 | 742 | 9.2 | 8.1 | 2.9 | 5.1 |
| According to WO 86/03122 | 219 | 38 | 39 | 1.4 | 34 |

*Thrombocytes
(1) Determined by the Bradford method (Biorad reagent, ref. 500-0006)
(2) β-thromboglobulin, determined by ELISA quantitative determination (Stago, ref. 0419)
(3) Platelet-derived growth factor, determined by an ELISA quantitative determination
(4) Transforming growth factor-β, determined after heating at 60° C. for 10 hours by the cloning technique in agar (Assoian et al., J. Biol. Chem., 258, 7555 (1983)).
(5) The value of the mitrogen activity corresponds to the dilution of the sample which induces, after stimulating for 24 hours, half of the maximum incorporation of tritiated thymidine by 3T3 clone A 31 cells at confluence.

I claim:

1. A method for obtaining a solution of platelet factors comprising:

activating thrombocytes by contacting the thrombocytes with a thrombocyte activator solution; and collecting platelet factors released by the thrombocytes as a result of said activating, wherein a liquid containing a suspension of thrombocytes is passed through a filter capable of retaining the thrombocytes, the activator solution is contacted with the thrombocytes retained on the filter and a filtrate containing the platelet factors in solution is separated by filtration while the thrombocytes remain retained on the filter.

2. The method according to claim 1, further comprising:

adding an appropriate washing solution to the thrombocytes retained on the filter before adding the activator solution; and removing the washing solution by filtration.

3. The method according to claim 1, wherein said method is performed under sterile conditions.

4. The method according to claim 1, wherein said filter delimits an upstream part and a downstream part of an enclosure, the upstream part being connected to at least one pipe equipped with appropriate means for opening and closing said at least one pipe and said at least one pipe connecting the upstream part to a reservoir containing a starting liquid, the downstream part being connected to at least one conduit that is equipped with appropriate opening and closing means and said at least one conduit making it possible to successively collect a filtrate of the starting liquid and the filtrate containing the platelet factors.

5. The method according to claim 4, wherein a reservoir containing the thrombocyte activator solution is connected to the upstream part and the thrombocyte activator solution is introduced into the upstream part to contact the thrombocytes.

6. The method according to claim 4, wherein said at least one pipe is connected to a reservoir containing a liquid for washing the thrombocytes and said at least one conduit is used to collect a filtrate of the washing liquid separate from the filtrate containing the platelet factors.

* * * * *